US00PP07940P

United States Patent [19]

Warriner

[11] Patent Number: Plant 7,940

[45] Date of Patent: Aug. 18, 1992

[54] ROSE PLANT JACSHUR

[75] Inventor: William A. Warriner, Tustin, Calif.

[73] Assignee: Bear Creek Gardens, Inc., Medford, Oreg.

[21] Appl. No.: 625,870

[22] Filed: Dec. 10, 1990

[51] Int. Cl.[5] ..... A01H 5/00

[52] U.S. Cl. ..... Plt./1

[58] Field of Search ..... Plt. 1, 22, 28

*Primary Examiner*—Howard J. Locker

*Attorney, Agent, or Firm*—Klarquist, Sparkman, Campbell, Leigh and Whinston

[57] ABSTRACT

A shrub class rose plant having bright red, simple flowers, vigorous upright habit of growth, dark green leathery foliage, resistance to powdery mildew and rust, high production of flowers throughout the growing season and ease of propagation by hardwood cuttings.

1 Drawing Sheet

The present invention relates to a new and distinct variety of rose plant of the shrub class which was originated by me by crossing the variety Razzle Dazzle, U.S. Plant Pat. No. 3,995, with an unnamed seedling.

The primary objective of this breeding was to produce a new rose variety having the bright red color of Razzle Dazzle and its dark leathery foliage combined with the shrub habit and heavy flower production of the unnamed seedling. The objective was substantially achieved along with other desirable improvements as evidenced by the following unique combination of characteristics which are outstanding in the new variety and which distinguish it from its parents, as well as from all other varieties of which I am aware:

1. Bright red, simple flower
2. Vigorous upright habit of growth
3. Dark green leathery foliage
4. Resistance to powdery mildew and rust
5. High production of flowers throughout the growing season
6. Ease of propagation by hardwood cuttings Asexual reproduction of this new variety by budding and by hardwood and softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent*—Razzle Dazzle, U.S. Plant Pat. No. 3,995.

*Pollen parent*—Unnamed seedling.

Classification:

*Botanical*—*rosa hybrida.*

*Commercial*—Shrub.

FLOWER

Observations made from specimens grown in a garden environment in Somis, Calif. in Sep. 1990.

Blooming habit: Continuous.

Bud:

*Size*—1 inch when the petals start to unfurl.

*Form*—Short, pointed ovoid.

*Color*—When sepals first divide, the bud color is Red Group 44B, with petals lightening to white at the petal bases. When half blown, the upper sides of the petals are Red Group 44A; and the lower sides of the petals are Red Group 44B, with the petals becoming lighter to white at the petal bases.

*Sepals*—Color: Green Group 138C. Surface texture: Covered with fine hairs. There are three lightly appendaged sepals. There are two unappendaged sepals with hairy edges.

*Receptacle*—Color: Green Group 137C. Shape: Apple. Size: Small (¼"×¼"). Surface: Glandular and hairy.

*Peduncle*—Length: Short (1½to 2"). Surface: Prickly, glandular. Color: Medium Green. Strength: Stiff, erect.

Bloom:

*Size*—Medium. Average open size is 3½ to 4 inches.

*Borne*—Singly and several together, in pyramidal clusters.

*Form*—When first open: Cupped. Permanence: Flattens.

*Petalage*—Number of petals under normal condition: 5 to 10.

*Color*—The upper side of the petals is Red Group 44A. The reverse side of the petals is Red Group 44B, changing to white at the point of attachment to the peduncle. The base of each petal has a white half moon at the point of attachment. The major color on the upper side is Red Group 44A.

*Variegations*—None.

*Discoloration*—No change in general tonality at the end of the first day: No change at the end of the third day.

*Fragrance*—Slight.

Petals:

*Texture*—Thick, leathery.

*Shape*—Round.
*Form*—Flat.
*Arrangement*—Imbricated. No Petaloids in the center.
*Persistence*—Drop off cleanly.
*Lastingness*—On the plant: Short, 3 to 4 days. As a cut flower: Short, 3 to 4 days.

Reproductive parts:
*Anthers*—Size: Medium. Quantity: Many. Color: Yellow. Arrangement: Regular around styles.
*Filaments*—Color: Reddish brown.
*Pollen*—Color: Lemon yellow.
*Styles*—Color: Reddish.
*Stigmas*—Color: Greenish white.

Form: Shrub.

Growth: Very vigorous, upright, branching.

Foliage:
*Number of leaflets on normal mid-stem leaves*—5.
*Size*—Large (6"×5").
*Quantity*—Abundant.
*Color*—New foliage: Reddish. Old foliage: Dark green.

Leaflets:
*Shape*—Broadly oval.
*Texture*—Upper side: Leathery, glossy.
*Edge*—Serrated.
*Serration*—Single, small.
*Petiole rachis*—Color: Reddish.

*Petiole underside*—Rough.
*Stipules*—Medium—¾"; bearded.
*Disease resistance*—Resistant to mildew and rust under normal growing conditions at Somis, Calif. Moderately susceptible to blackspot in tests in Baton Rouge, La.

Wood:
*New wood*—Color: Reddish. Bark: Smooth.
*Old wood*—Color: Green. Bark: Smooth.

Prickles:
*Quantity*—On main canes from base: Ordinary. On laterals from main canes: Ordinary.
*Form*—Medium, hooked downward.
*Color when young*—Red.

Small prickles:
*Quantity*—On main stalks: Few. On laterals: Many.
*Color*—Brown.

I claim:

1. A new and distinct variety of rose plant of the shrub class, substantially as herein shown and described, characterized particularly as to novelty by the unique combination of its brigh red, simple flower, its vigorous upright habit of growth, dark green leathery foliage, resistance to powdery mildew and rust, high production of flowers, and its ease of propagation from hardwood cuttings.

* * * * *

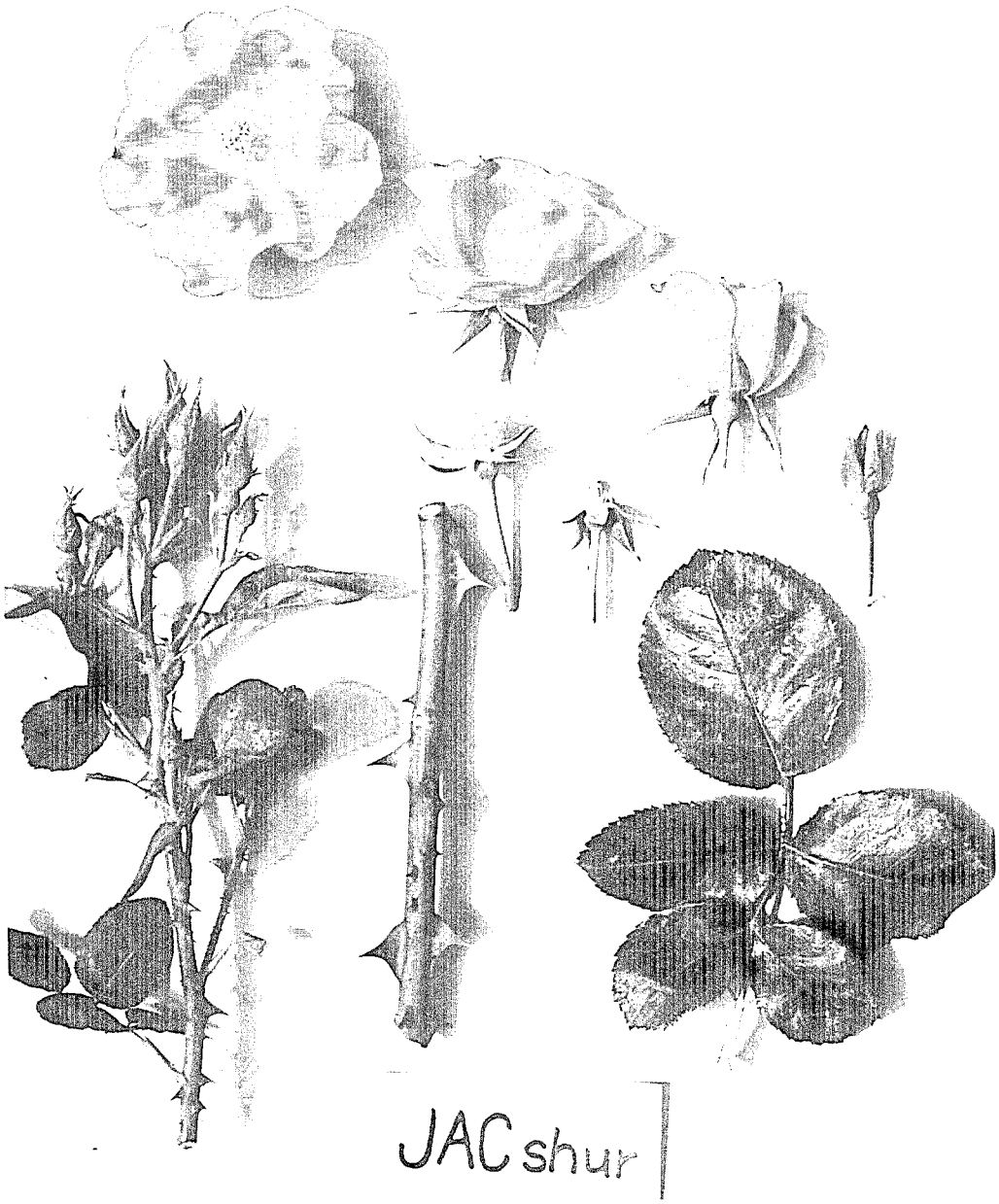
JACshur